United States Patent [19]

Sakurai et al.

[11] Patent Number: 4,553,424

[45] Date of Patent: Nov. 19, 1985

[54] METHOD FOR DETECTING AN OXYGEN CONCENTRATION AND A METHOD FOR CONTROLLING AN AIR-TO-FUEL RATIO BASED ON THE DETECTED OXYGEN CONCENTRATION

[75] Inventors: Shigenori Sakurai; Takashi Kamo; Shirou Kimura, all of Toyota, Japan

[73] Assignee: Toyota Jidosha Kabushiki Kaisha, Toyota, Japan

[21] Appl. No.: 477,845

[22] Filed: Mar. 22, 1983

[30] Foreign Application Priority Data

Mar. 23, 1982 [JP] Japan ................................. 57-45902
Apr. 5, 1983 [JP] Japan ................................. 58-56365

[51] Int. Cl.$^4$ ............................................. G01N 27/04
[52] U.S. Cl. .................................. 73/27 R; 73/119 A
[58] Field of Search .................. 73/27 R, 116, 119 A; 123/440; 364/573

[56] References Cited

U.S. PATENT DOCUMENTS 4,149,120 4/1979 Richter ........................... 364/573 X
4,244,918 1/1981 Yasuda et al. ..................... 73/27 R X

*Primary Examiner*—Jerry W. Myracle

*Attorney, Agent, or Firm*—Oblon, Fisher, Spivak, McClelland & Maier

[57] ABSTRACT

A method for detecting the oxygen concentration of a gas to be measured is disclosed using the limiting current type oxygen sensor. The method is characterized in that the relationship of an inclined straight line between the voltages applied to the oxygen sensor and the currents outputted therefrom is determined in such a manner that the inclined straight line may pass through the flat portions of the limiting current in the voltage-current characteristics curves at the different oxygen concentrations. The relationship between the outputted currents and the oxygen concentrations at the flat portion is such that when a given magnitude of voltage is applied to the oxygen sensor to cause it to output a current, a voltage which corresponds to this current at the inclined straight line is determined. The voltage thus determined is applied to the oxygen sensor to cause it to output a current. The oxygen concentration is determined from the current thus outputted with reference to the outputted current-oxygen concentration conversion straight line. There is also disclosed a method for controlling the air-to-fuel ratio of a gas from an engine using the above voltage-current characteristic curves, inclined straight line and outputted current-oxygen concentration.

6 Claims, 6 Drawing Figures

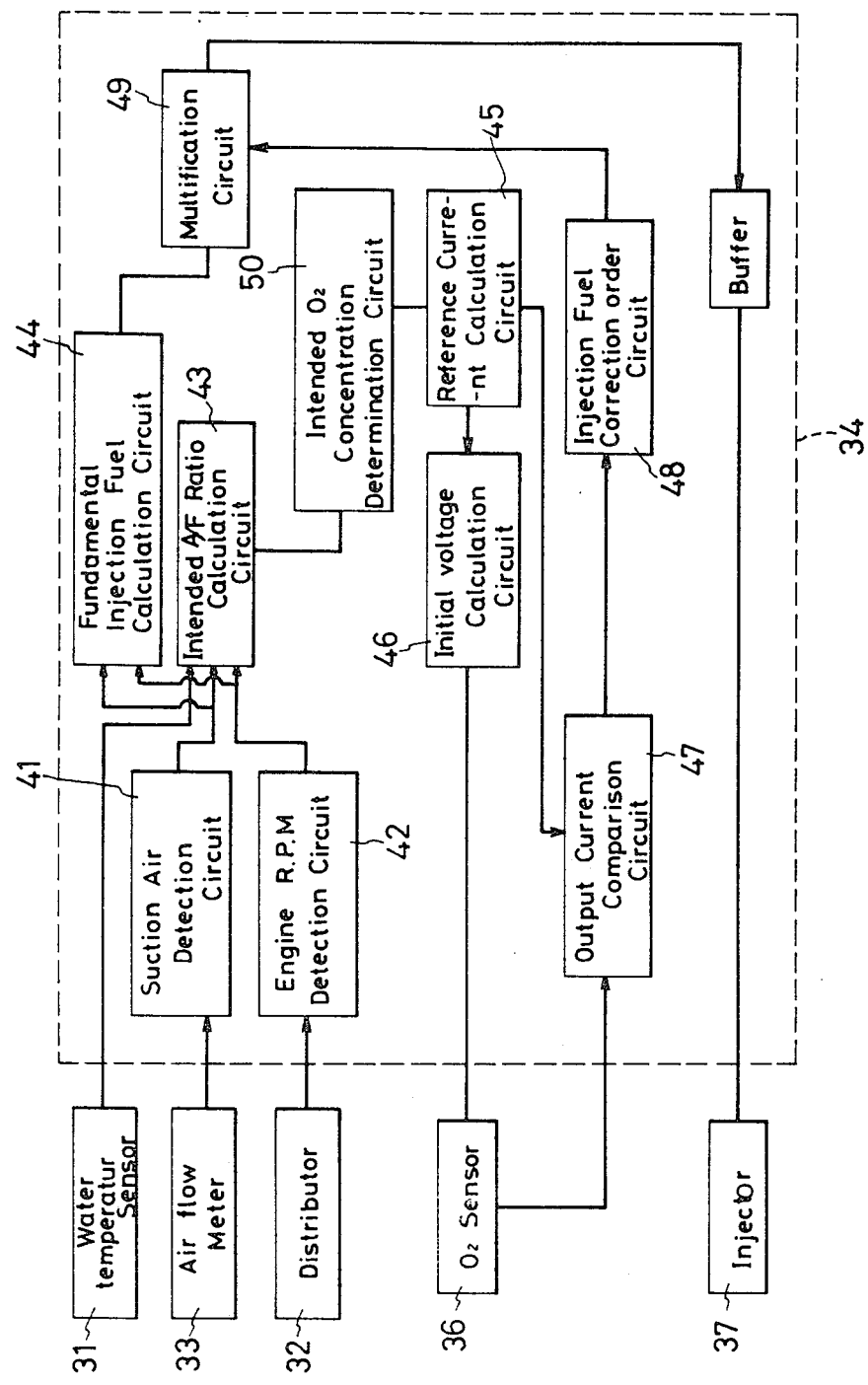

METHOD FOR DETECTING AN OXYGEN CONCENTRATION AND A METHOD FOR CONTROLLING AN AIR-TO-FUEL RATIO BASED ON THE DETECTED OXYGEN CONCENTRATION

BACKGROUND OF THE INVENTION

1. Field of the Invention:

The present invention relates to a method of detecting the concentration of oxygen in a gas to be measured, and it also relates to a method of controlling the air-to-fuel ratio in an engine based on the detected oxygen concentration. More specifically, the invention relates to a method of detecting the concentration of oxygen in a gas to be measured using a limiting current type oxygen sensor, and a method of controlling the air-to-fuel ratio in an engine based on the detected oxygen concentration.

2. Description of the Prior Art

Limiting current type oxygen sensors have been conventionally employed for detecting the concentration of oxygen in a gas to be measured. According to the limiting current type oxygen sensors, an oxygen sensor element body is made of an oxygen-ion permeable solid electrolyte with electrode plates being provided on the opposite surfaces of the element body, and with one of the electrode plates (a negative electrode) coated with a porous ceramic layer thicker than that covering the other (a positive electrode).

When in use, the oxygen sensor having the oxygen sensor element thus constituted therein is mounted on a specific place in such a manner that the oxygen sensor element may be brought into contact with a gas to be measured. The application of voltage to the electrode plates causes a limiting current to flow through the oxygen sensor element depending upon the concentration of oxygen in the gas. Thus, the intensity of this current outputted from the oxygen sensor element is measured to detect the concentration of oxygen in the gas to be measured.

The conventional method for detecting the oxygen concentration using such a limiting current oxygen sensor will be described below with reference to FIG. 1.

FIG. 1 is a graph illustrating the relationship between the voltage applied to the oxygen sensor and the current outputted from it. The curves 1, 2 and 3 represent the voltage-electric current characteristics respectively when the concentrations of oxygen in the gases to be measured are 1%, 5%, 10%.

When a voltage is applied to the opposite electrode plates of the limiting current type oxygen sensor element, oxygen in the gas to be measured is ionized at the negative electrode to permeate through the oxygen sensor element toward the positive electrode. With the increase in the voltage applied to the oxygen sensor element, the output electric current increases correspondingly or proportionally. In FIG. 1, reference numerals 1a, 2a, 3a represent first stage leading edges (portions) of the curves 1, 2, 3 in the respective oxygen concentrations. When the voltage applied to the oxygen sensor element exceeds a certain value, the amount of the permeating oxygen from the negative electrode to positive electrode is limited because the negative electrode of the sensor element is covered with the porous ceramic layer. Thus, when the applied voltage is further increased, the current obtained is kept constant, i.e., the so-called limiting current is outputted. Reference numerals 1b, 2b, 3b represent the flat portions of the characteristic curves 1, 2, 3 at the different oxygen concentrations respectively. The values of the limiting current proportionally vary with the oxygen concentrations, and further the range of the voltage which give rise to a limiting current depends upon the oxygen concentration. When the voltage applied becomes larger than this range producing the limiting current, the outputted electric current begins to increase again with the applied voltage. Reference numerals 1c, 2c, 3c represent the second stage leading edges (portions) of the characteristic curves at the different oxygen concentrations respectively.

Assume that a voltage falling within the voltage range which gives rise to the current intensities at the flat portions 1b, 2b and 3b at all the different oxygen concentrations respectively is selected and that such a voltage is applied to the oxygen sensor element. Then, the oxygen concentration in a gas to be detected can be determined by the measurement of the outputted current because the oxygen sensor element outputs the limiting current in proportion to the oxygen concentration. However, the voltage ranges giving the flat portions at the different oxygen concentrations of the characteristic curves shift little by little.

For this reason, when a certain amplitude of voltage shown at the vertical line "B" in FIG. 1 is applied to the opposite electrodes of the limiting current type oxygen sensor, and the oxygen concentration is kept, for instance, at 1%, 5% or 10%, the current with the intensity at an ordinate of the intersecting point between the line "B" and the characteristic curve 1, 2 or 3 is outputted from the oxygen sensor. The relationship between the outputted electric current and the different oxygen concentrations is preliminarily determined. Then, the concentration of oxygen contained in a gas to be measured is detected with reference to the preliminarily determined relationship between the outputted current and the oxygen concentration. According to the conventional method, however, since the voltage applied to the oxygen sensor element is set constant, it is not necessarily possible to detect with accuracy the concentration of oxygen, because in some cases, the limit current corresponding to the specific oxygen concentration cannot be outputted.

For instance, when the voltage applied is set at the constant value "$x_1$" as shown in the vertical line "B", if the oxygen concentration is 5% or 10% (the characteristic curves 2 and 3), the oxygen sensor outputs an accurate limiting current intensities $y_1$ and $y_2$ at these oxygen concentrations because the line "B" intersects the characteristic curve 2 or 3 at flat portion 2b, or 3b i.e., the applied voltage falls within the specified ranges giving rise to flat portions 2b and 3b. On the other hand, when the oxygen concentration is 1%, the vertical line "B" intersects the curved portion, or the second stage leading edge (portion) 1c, not at the flat portion 1b. Consequently, the intensity of the electric current outputted from the oxygen sensor becomes larger than that of the limiting current $y_{12}$. Thus, the oxygen sensor gives an inaccurate measurement of the oxygen concentration in the gas to be measured.

FIG. 2 illustrates in a one dotted chain line "$\overline{B}_1$" the relationship between the electric current outputted from the oxygen sensor and the oxygen concentration when the voltage applied to the sensor element is set constant as shown by "B" of FIG. 1. The one dotted chain line "$\bar{B}_1$" corresponds to the state when the line "B" is shifted to the right as shown in FIG. 1. To the contrary, the two dotted chain line $\bar{B}_2$ corresponds to the state that the line B is shifted to the left different from the line B in FIG. 1.

The outputted electric current is converted into the oxygen concentration based on this curve "$\bar{B}(\bar{B}_1$ or $\bar{B}_2)$". From FIG. 2, it is seen that the lineality of the outputted current-oxygen concentration conversion line "$\bar{B}$" is shifted upwardly at the low concentration, while the lineality at more than 10% of the oxygen concentration is shifted downwardly in the line "$\bar{B}_2$" because the flat portion of the corresponding characteristic curve is deviated to the right in FIG. 1 and accordingly, the current outputted at the applied voltage x becomes higher or lower than the limiting current.

In this way, since the range in the oxygen concentration which produces their limiting currents becomes restricted when the voltage applied to the oxygen sensor is set constant, the conventional method cannot give accurate measurement of the oxygen concentrations when they vary over a wide range.

In addition, the ranges in the voltage which give rise to the flat portions of the limiting current in the characteristic curves may differ from one another due to the variance in the characteristics of the different oxygen sensors. The above-described conventional method cannot satisfactorily dispose of such a variance.

Another problem is the difficulty of obtaining satisfactory control of the air-to-fuel ratio in such a system where the outputted electric current proportional to the oxygen concentration in a gas to be measured is detected using the limiting current type oxygen sensor, and where a control signal based on this outputted current is inputted to the fuel supply means to control the air-to-fuel ratio in the engine.

In order to eliminate the problems encountered by the conventional method, it is considered preferable to widen the flat portions of the characteristic curves. However, the present level of technology makes this difficult.

SUMMARY OF THE INVENTION

Accordingly, one object of the present invention is to provide a method for measuring an oxygen concentration in a gas to be detected using the limiting current type oxygen sensor, which method is free from the drawbacks encountered by the conventional method of applying a constant voltage to the oxygen sensor.

More specifically, the object of the invention is to provide a method for measuring an oxygen concentration in a gas to be detected using the limiting current type oxygen sensor, which method can give accurate measurement of the oxygen concentration in the gas over a wide range of the oxygen concentration.

Another object of the present invention is to provide a method for measuring the oxygen concentration of a gas to be detected using the limiting current type oxygen sensor, which method ensures the lineality between the electric current output from the oxygen sensor and the oxygen concentration being detected.

Still another object of the present invention is to provide a method for measuring the oxygen concentration of a gas to be detected using the limiting current type oxygen sensor, which method can measure accurately the concentration of the oxygen in the gas despite variances in the oxygen sensors.

A further object of the present invention is to provide a method for controlling an air-to-fuel ratio of an engine using the limiting current type oxygen sensor.

According to the method of the present invention which uses the limiting current type oxygen sensor, the linear relationship between the voltage applied to the oxygen sensor and the electric current (limiting current) outputted from it is determined by a linear function which is adapted to pass through the flat (limiting current) portions of the voltage-current characteristic curves at the various oxygen concentrations, then the relationship between the outputted current and the oxygen concentration is determined with reference to the above linear relationship thus determined and the characteristic curves. A given magnitude of voltage is then applied to the oxygen sensor element, so that the intensity of the current outputted from the element is measured. The voltage is corrected to an appropriate voltage with reference to the outputted current and the above linear function at which the oxygen sensor produces the limiting current, and the corrected voltage is then applied to oxygen sensor element to obtain the limiting current at this corrected voltage. Lastly, the intensity level of the outputted electric current is converted to the oxygen concentration with reference to the linear relationship between the current outputted from the oxygen sensor element and the oxygen concentrations under the limiting current-producing conditions.

Further, according to the present invention, the oxygen concentration as determined above in a gas to be detected of an engine on given conditions is compared with that of the intended air-to-fuel ratio of the engine, so that an amount of a fuel to be supplied to the engine is controlled, whereby the actual air-to-fuel ratio reaches the intended ratio.

BRIEF DESCRIPTION OF THE DRAWINGS

These and other objects and features of the present invention will be appreciated well by a reading of the following description of the invention in conjunction with the attached drawings in which:

FIG. 6 is a flow chart illustrating the method for controlling the air-to-fuel ratio according to the present invention.

DETAILED DESCRIPTION OF THE INVENTION

Figure 1:
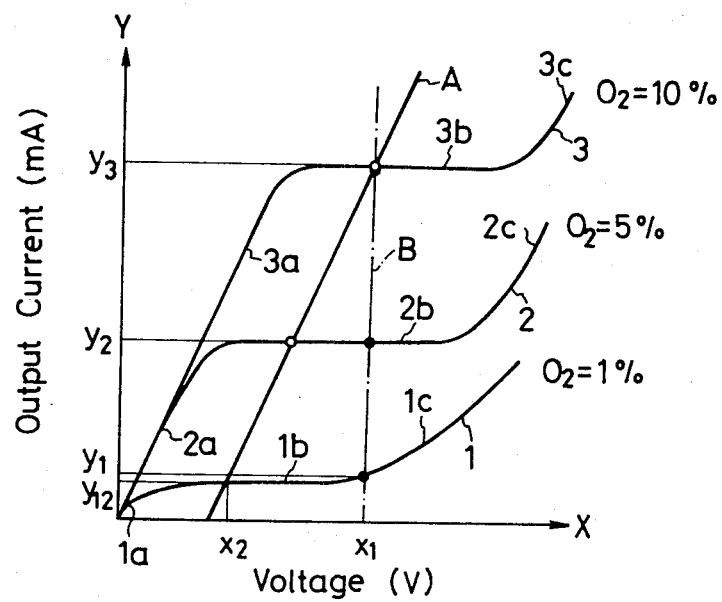
FIG. 1 is a diagram illustrating the characteristic curves between the voltage applied to an oxygen sensor element and electric current outputted from it in the limiting current type oxygen sensor, and a voltage-current inclined straight line.
Figure 2:
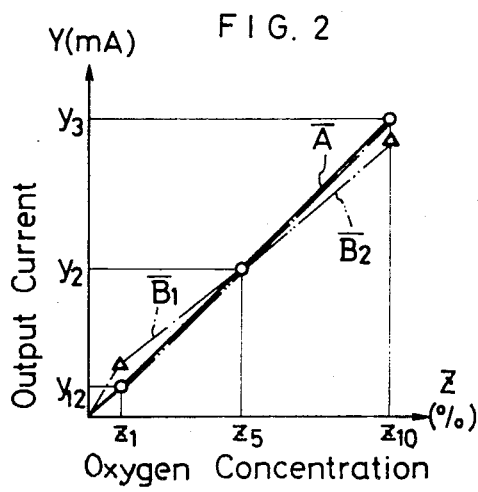
FIG. 2 is a diagram illustrating the relationship between the current outputted from the oxygen sensor element and the oxygen concentration.

The present invention will be described in detail with reference to the attached drawings wherein FIG. 1 shows the relationship between the voltage applied to the oxygen sensor of a limiting current type and the electric current outputted from it at various oxygen concentrations is determined as characteristic curves. Then, an inclined straight line A which passes through the flat portions (limiting current portions) of the voltage-current characteristic curves at these various oxygen concentrations is determined. Further, the outputted current-oxygen concentration conversion line $\overline{A}$ as shown in FIG. 2, is determined.

Next, the current outputted from the oxygen sensor element by applying a certain magnitude of voltage to it is outputted, and thereafter the above-applied voltage is corrected to a voltage by using the above inclined straight line relationship between the voltage and current. The voltage, as corrected, is applied to the oxygen sensor element to output a current at this voltage from it, and the intensity of the current thus outputted is converted to the oxygen concentration of a gas to be detected with reference to the linear relationship between the current and the oxygen concentrations as shown by $\overline{A}$ in FIG. 2.

An inclined straight line between the voltage and current and an outputted current-oxygen concentration conversion straight line to be used for performing the method according to the present invention will be explained below.

In FIG. 1, a symbol "A" represents an inclined straight line having the voltage "X" applied to the oxygen sensor element and the current "Y" outputted from it as its variables, the inclined straight line being expressed by a linear function: $Y = mX + n$ (m,n=const. m>0,n<0). The linear function is so determined that it may pass through the flat portions $1b$, $2b$, $3b$ of the characteristic curves 1, 2, 3 at the different oxygen concentrations. In other words, this linear function is so determined that the voltage "X" to be applied to the oxygen sensor element falls within the voltage range which gives rise to the flat portions $1b$, $2b$, $3b$. Commonly, the voltage to be applied to the oxygen sensor element may be set at 0.2 to 1.0 V. The constant "m" may be appropriately selected by changing a variable resistance provided in the oxygen sensor or the like, but it is preferable to set it substantially at the same inclination as that of the leading edges (portions) $1a$, $2a$, $3a$ of the characteristic curves 1, 2, 3. When the constant "m" is set at this inclination of the leading portions, even if the flat portion of the characteristic curve shifts gradually with the increase in the oxygen concentration, the inclined straight line "A" can be extrapolated correspondingly so that the straight line "A" will pass through the flat portions of the characteristic curves from the lower to the higher concentrations.

Figure 4:
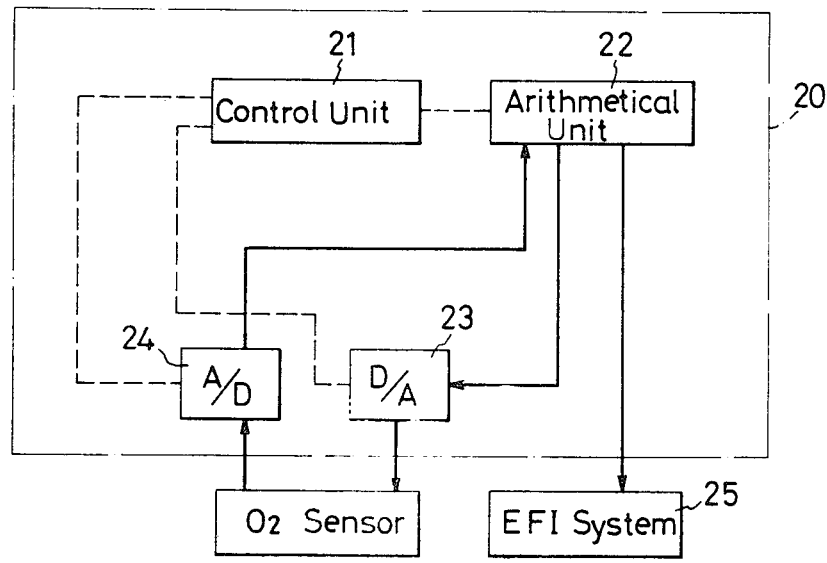

The relationship of the inclined straight line "A" $(Y=mX+n)$ between the voltage and the current is memorized in a memory of a controller 20 shown in FIG. 4 by an appropriate means such as a table method using IC memory, a function generator or the like, and when necessary, the memorized relationship is used for the measurement of the oxygen concentration in the gas.

From the characteristic curves 1, 2, 3 and the inclined straight line "A", the outputted current-oxygen concentration conversion line "$\overline{A}$" of FIG. 2 is determined in such a manner that at the intersections between the characteristic curves 1, 2, 3 and the inclined straight line "A" are determined the intensities of the outputted currents, $y_{12}$, $y_2$, $y_3$, and the corresponding oxygen concentrations, $z_1$, $z_5$, $z_{10}$, these values of the currents and oxygen concentrations are plotted in an ordinate and abscissa respectively as shown in FIG. 2, and lines are drawn by connecting the plotted points. All the values of the outputted currents of the conversion straight line "$\overline{A}$" are ones on limiting current state. Accordingly, the lineality of this straight line "$\overline{A}$" can be assured over a wide range from the lower to the higher oxygen concentrations.

The relationship of the straight line "$\overline{A}$" is also inputted to a memory of the controller 20 as a linear function "$Y=a\cdot Z$ (a:constant)" similarly to the relationship of the straight line "A", and when necessary, the memorized relationship is used for the measurement of the oxygen concentration.

Figure 3:
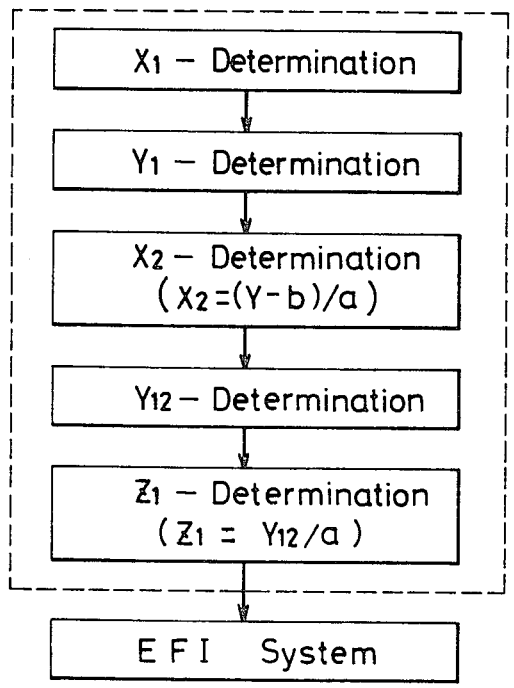
FIGS. 3 and 4 are flow charts illustrating a method according to the present invention.

The controller 20 comprises a control unit 21, an arithmetical unit 22, a D/A convertor 23 and an A/D convertor 24. The control unit 21 is adapted to control the arithmetical unit 22, D/A convertor 23 and A/D convertor 24 in accordance with the sequence as shown in FIG. 3, whereby a signal is outputted to the D/A convertor 23 and, for example, an engine fuel injection (EFI) system. The D/A convertor is adapted to set the voltage $x_2$ to be applied to the oxygen sensor. The intensity $y_1$ of the current outputted from the oxygen sensor is inputted to the A/D convertor 24 for the A/D conversion. Then, the converted signal is inputted to the arithmetical unit 22 wherein $x_2$ is determined based on the inputted signal with reference to the linear function: $X=(Y-b)/a$. Further, the intensity $y_{12}$ of the current outputted when the voltage $x_2$ is applied to the oxygen sensor is inputted to the A/D convertor 24, and then the converted signal is inputted to the arithmetical unit 22 wherein the oxygen concentration of a gas to be detected is obtained with reference to the linear function: $Z=y_{12}/a$.

The method according to the present invention is performed with reference to or on the basis of the characteristic curves 1, 2, 3, the inclined straight line "A", and the conversion straight line "$\overline{A}$". The invention will be explained more specifically by way of example referring to the method of detecting the concentration of oxygen in a exhaust gas from an internal combustion engine.

An oxygen sensor of the limiting current type is mounted on an exhaust pipe of the internal combustion engine in such a manner that an oxygen sensor element may be brought into contact with the exhaust gas from the engine. Then, a certain magnitude of voltage "$x_1$" is applied to the oxygen sensor element. This voltage is usually set at a certain value from 0.2 to 1.0 V at which the oxygen sensor is conventionally impressed. As shown in FIG. 1, when the oxygen concentration is 1.0% (characteristic curve 1), the sensor element outputs the current "$y_1$". The signal of output current "$y_1$" is inputted to the controller 20 in which the relationship of the straight line "A" is preliminarily inputted, so that the voltage "$x_2$" is determined. Thus, the voltage to be applied to the oxygen sensor element is corrected from the voltage "$x_1$" to "$x_2$". Then, the corrected voltage "$x_2$" is applied to the oxygen sensor element, and ultimately the oxygen concentration is determined on the basis of the current $y_{12}$ outputted from the element with reference to the relationship of the conversion straight line "$\overline{A}$" in FIG. 2. The above-mentioned measuring steps are taken as one cycle of the measurement of the oxygen concentration. This cycle is repeated 10 to 0.1 times per second to continuously detect the oxygen concentration in the exhaust gas.

When the oxygen concentration in the exhaust gas is 10%, the application of the voltage "$x_1$" causes the oxygen sensor element to output the current "$y_3$". In this case, no correction of the voltage is required because the voltage at the line "A" at the limiting current "$y_3$" is "$x_1$". With no voltage correction, the oxygen concentration "$z_{10}$" is determined from the current "$y_3$" with reference to the conversion line "$\overline{A}$".

The voltage initially applied to the sensor element is not necessarily restricted to a specific one, but it is set at an appropriate magnitude within the voltage range at which the oxygen sensor element is ordinarily impressed. Further, the corrected voltage may be applied to the oxygen sensor element by a commonly employed circuit comprising the microcomputer, D/A convertor, output amplifier, etc.

As mentioned above, according to the present invention, voltage to be applied to the oxygen sensor element is controlled to the specific range in which the limiting currents are always outputted at various oxygen concentrations. Therefore, it is possible to accurately detect the oxygen concentration based on the current outputted from the sensor element.

In addition, since if the limiting current characteristics of the oxygen sensor elements vary, the voltage-current inclined straight line can be determined to dispose of such variance through data analysis, the lineality of the straight line $\overline{A}$ can be assured.

The method according to the present invention is applicable not only to the detection of the oxygen concentration of the exhaust gas in the internal combustion engine as mentioned above, but also to the detection of the oxygen concentration of the exhaust gas from the boiler, furnace or the like of the conventional fuel combustion type.

According to another aspect of the present invention, it is possible to accurately control the air-to-fuel ratio of an engine using the limiting current type oxygen sensor in accordance with the above-mentioned method.

First, the air-to-fuel ratios as desired or intended on various driving conditions are determined (these air-to-fuel ratios are referred to hereinafter as "intended air-to-fuel ratios"). Then, the voltage to be applied to the sensor element is varied depending upon the intended air-to-fuel ratio, and the intensity of the current outputted from the sensor element, when the voltage is applied, is compared with that of the reference current at the intended air-to-fuel ratio, so that the air-to-fuel ratio is controlled by adjusting the supply of the fuel based on a comparison signal.

More particularly, the latter method according to the present invention is performed as follows:

First, the inclined straight line "A" and the outputted current oxygen concentration conversion straight line "$\overline{A}$" are determined as stated in connection with the former method. Then, the intended oxygen concentrations (corresponding to the intended air-to-fuel ratio) in the exhaust gas to be measured from the engine are determined with reference to the respective driving conditions, and the voltage to be applied to oxygen sensor and the reference current in the case of the intended oxygen concentration are determined with reference to the outputted current-oxygen concentration conversion straight line "$\overline{A}$" and the inclined straight line. Next, the voltage thus determined is applied to the sensor element so as to cause the sensor element to output a current, and then the intensity of the outputted current is compared with that of the reference current so as to obtain a comparison signal which is used to control the supply of fuel.

The air-to-fuel controlling method according to the present invention will be explained more in detail with reference to the drawings, especially FIGS. 5 and 6.

Figure 5:
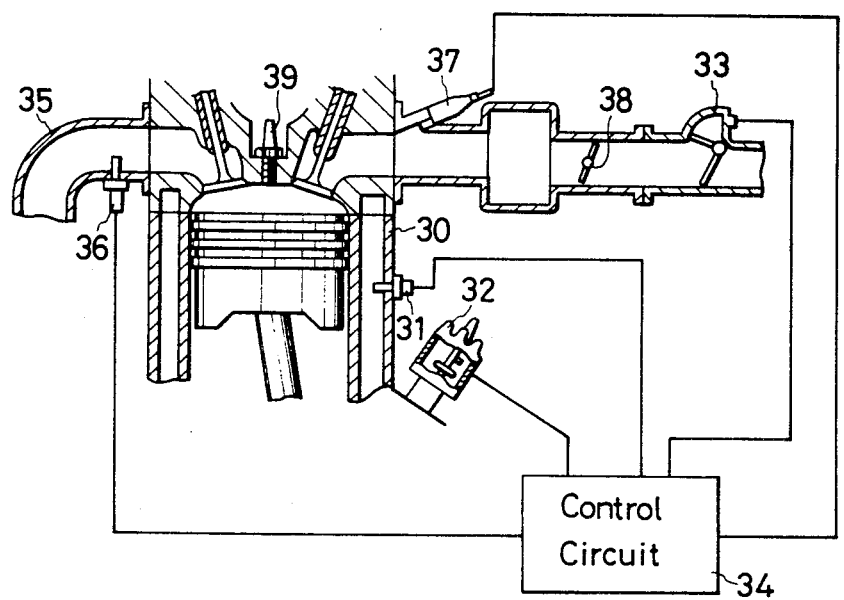
FIG. 5 is a schematical view of an air-to-fuel controlling system in an engine.

FIG. 5 schematically shows the principal parts of a system for controlling the air-to-fuel ratio according to the present invention in which reference numerals 30, 31, 32, 33, denote an engine body, a water temperature sensor for detecting the temperature of the engine cooling water, a distributor for detecting the number of revolutions of the engine and an air flow meter respectively. The detection signals from the water temperature sensor 31, distributor 32 and the air flow meter 33 are inputted to the control circuit. To the control circuit 34 is electrically connected an injector 37 and an oxygen sensor 36 attached to the exhaust pipe 35. The control signal from the control circuit 34 is inputted to the oxygen sensor 36, while the signal for controlling the fuel injection is inputted to the injector 37. Reference numerals 38 and 39 denote a throttle valve and an ignition plug respectively.

In such an internal combustion engine thus constituted, the air-to-fuel ratio is controlled in accordance with the systematic sequence as shown in FIG. 6.

First, the amount of the air sucked into the engine is detected by means of the air flow meter 33 under a certain driving condition, while the number of revolutions of the engine is detected by means of the distributor 32. The signals as to the sucked air amount, as detected by circuit 41, and the number of engine revolutions, as detected by the circuit 42, as well as the signal as to the engine cooling water temperature sensed by the water temperature sensor 31 are inputted to an arithmetic operation circuit 43 for the intended air-to-fuel, wherein the intended air-to-fuel ratio (A/F) under the driving condition is determined. Simultaneously, the fundamental volume of the fuel to the injector 37 is determined by circuit 44 from the dectection signals as to the sucked air amount and the number of engine revolutions. The intended air-to-fuel ratio is converted to the intended oxygen concentration by an intended $O_2$ concentration determination circuit 50. This conversion is done in such a manner that the intended air-to-fuel ratio determined based on the detection signals from the sensors is processed with reference to a function memorized in the circuit 50 which function is adapted to make the conversion from the intended air-to-fuel ratio to the intended oxygen concentration, and which function is preliminarily inputted in a memory.

When the intended oxygen concentration is determined, the current (reference current) corresponding to the intended oxygen concentration is determined by circuit 45 with reference to the signal as to the intended oxygen concentration and the above-memorized conversion straight line "$\overline{A}$". Then, the voltage to be applied to the oxygen sensor element is determined from the reference current thus obtained and the inclination straight line "A" preliminarily inputted in the memory by means of circuit 46.

Next, the voltage thus determined is applied to the oxygen sensor 36, so that the sensor outputs current (outputted current). The intensity of the outputted current and that of the reference current are compared with each other in the comparison circuit 47. In this case, when the outputted current is smaller than the reference current, a correction signal for reducing the fundamental fuel injection amount is outputted from a fuel injection correcting order circuit 48, and then inputted to the injection 37 through the modification circuit 49 in order to reduce the fuel injection amount. Thereby, the fuel amount from the injection is reduced and accordingly the oxygen concentration in the exhaust gas is increased. The comparison in intensity between the reference current and the outputted current as well as the control step for reducing the fuel supply are taken as one cycle, and this cycle is repeated so as to approach the intensity of outputted current to the reference one, thereby so controlling the system that the actual air-to-fuel ratio may reach the intended one.

When the outputted current is larger than the reference one, a correction signal for increasing the fuel injection amount is inputted to the injector 37. By the repeated comparison in intensity between the reference current and the outputted one as well as the repeated injection, fuel increasing steps are performed so that the actual air-to-fuel ratio may reach the intended ratio.

As mentioned above, the air-to-fuel controlling method according to the present invention automatically enables the determination of a voltage to be applied to the oxygen sensor element in accordance with the intended oxygen concentration or the intended air-to-fuel ratio.

Further, the more accurate control for the air-to-fuel ratio can be attained due to the advantages stated in connection with the former oxygen concentration determination method.

The present invention has been described in the specific forms of the embodiments, but it is to be understood that modifications, changes, and variations of the invention will occur to those skilled in the art to which the invention pertains without departing from the spirit of the invention and scope of the claims.

What is claimed as new and desired to be secured by letters patent of the United States is:

1. A method for measuring the concentration of oxygen in a gas to be detected using a limiting current type oxygen sensor which is adapted to output a current in response to the oxygen concentration of the gas and the characteristic curve between voltage applied to the oxygen sensor and the current outputted therefrom of which consists of a first leading edge portion that increases in current intensity level with the increase in the voltage applied to the oxygen sensor within a voltage range less than a first magnitude of voltage, a flat portion of a substantially constant current intensity level from the first magnitude to a second magnitude of voltage even with the increase in voltage, and a second leading edge portion for a voltage more than the second magnitude, and said limiting current type oxygen sensor having the voltage range of from the first to second leading portions which gives rise to the flat portions of the voltage-current characteristic curves shift depending on the different oxygen concentrations of the gas, which method comprising the steps: determining the position and slope relationships of an inclined straight line having voltage applied to the oxygen sensor and the current outputted from the oxygen sensor as its variables that the voltages applied to the oxygen sensor and taken along the inclined straight line at different oxygen concentrations fall within the specified voltage range which gives rise to the flat portion at each of said oxygen concentrations;

determining the relationship of an outputted current-oxygen conversion straight line with reference to the voltage-current characteristic curve and the inclined straight line;

inputting a given magnitude of initial voltage to the oxygen sensor to cause it to output a current;

correcting the initial voltage based on the outputted current with reference to the inclined straight line;

inputting the corrected voltage to the oxygen sensor to cause it to output a current; and determining the concentration of oxygen in the gas from the current thus outputted from the application of the corrected voltage with reference to the outputted current-oxygen concentration conversion straight line.

2. The method claimed in claim 1, wherein the slope of the inclined straight line is substantially the same as that of said leading edge portions of the voltage-current characteristic curves.

3. The method claimed in claim 1, wherein the magnitude of the initial voltage is from 0.2 to 1.0 V.

4. The method claimed in claim 1, 2 or 3, wherein the oxygen concentration is determined by the system which comprises said limiting current type oxygen sensor, an A/D convertor which is adapted to convert an analogue signal from the oxygen sensor to a first digital signal, an arithmetical unit which is adapted to memorize the relationships of the inclined straight line and the outputted current-oxygen concentration conversion straight line, to make operation, based on said memorized relationships, of the digital signal to generate a second digital signal, and to output a signal to an external system, and a D/A convertor which is adapted to convert the second digital signal to an analogue signal and output the analogue signal thus converted to the oxygen sensor, and a control unit for controlling the A/D convertor, the arithmetic unit and the D/A convertor so as to perform the measurement of the oxygen concentration of the gas.

5. The method claimed in claim 4, wherein the external system is an EFI system.

6. The method claimed in claim 2, wherein the magnitude of the initial voltage is from 0.2 to 1.0 V.

* * * * *